United States Patent [19]

Chodorow

[11] Patent Number: 4,807,752
[45] Date of Patent: Feb. 28, 1989

[54] DENTAL FLOSS HOLDERS AND PACKAGE ASSEMBLY OF SAME

[75] Inventor: Ingram S. Chodorow, Upper Saddle River, N.J.

[73] Assignee: Placontrol Corporation, Montvale, N.J.

[21] Appl. No.: 819,906

[22] Filed: Jan. 21, 1986

[51] Int. Cl.⁴ .................... A61B 19/02; A61C 15/00
[52] U.S. Cl. .................... 206/63.5; 206/438; 206/467; 206/480; 206/485; 206/820; 132/323; 132/324
[58] Field of Search ............ 206/37, 38, 63.3, 65.5, 206/461, 467, 470, 474, 473, 368, 369, 601, 602, 820, 438, 49, 339, 485, 495, 526; 132/91, 92 R, 92 A, 93; D28/64

[56] References Cited

U.S. PATENT DOCUMENTS

| | | | |
|---|---|---|---|
| 1,559,320 | 10/1925 | Hirsh | 192/93 |
| 2,083,398 | 6/1937 | Rohland | 206/63.5 |
| 2,612,177 | 9/1932 | Footer | 206/368 |
| 2,901,100 | 8/1959 | Mueller et al. | 206/485 |
| 3,094,209 | 6/1963 | Krupp | 206/63.5 |
| 3,136,416 | 6/1964 | Goldrosen | 206/372 |
| 3,174,621 | 3/1965 | Watson | 206/470 |
| 3,285,404 | 11/1966 | Spinney | 206/526 |
| 3,438,486 | 8/1966 | Pinkas | 206/820 |
| 3,463,309 | 8/1969 | Szostel | 206/470 |
| 3,571,920 | 3/1971 | Berg | 206/820 |
| 3,930,059 | 12/1975 | Wells | 132/91 |
| 3,952,870 | 4/1976 | Garnier | 206/63.5 |
| 4,016,892 | 4/1977 | Chodorow | 132/91 |
| 4,016,972 | 4/1977 | Szamborski | 206/470 |
| 4,034,770 | 7/1977 | Trecker | 206/63.5 |
| 4,162,687 | 7/1979 | Lorch | 132/91 |
| 4,222,708 | 12/1983 | Birnholz | 206/820 |
| 4,456,123 | 6/1984 | Russel | 206/820 |
| 4,471,874 | 9/1984 | Morane | 206/380 |
| 4,504,229 | 3/1985 | Garito et al. | 433/225 |
| 4,549,649 | 10/1985 | Roshdy | 206/63.3 |
| 4,550,471 | 11/1985 | Kray | 132/93 |
| 4,579,221 | 4/1986 | Corella | 206/63.3 |

Primary Examiner—David T. Fidei
Attorney, Agent, or Firm—Rosen, Dainow & Jacobs

[57] ABSTRACT

A plurality of dental floss holders, each formed of a length of floss with gripping elements are aligned in succession with the floss of each being part of a continuous strand that is severable between holders, and with each two adjacent gripping elements of adjacent holders being separable parts of an initially unitary component. Also disclosed is an assembly of parallel disposed floss holders releasably joined together in dispenser packages and other assemblies of packaged dental floss holders.

21 Claims, 16 Drawing Sheets

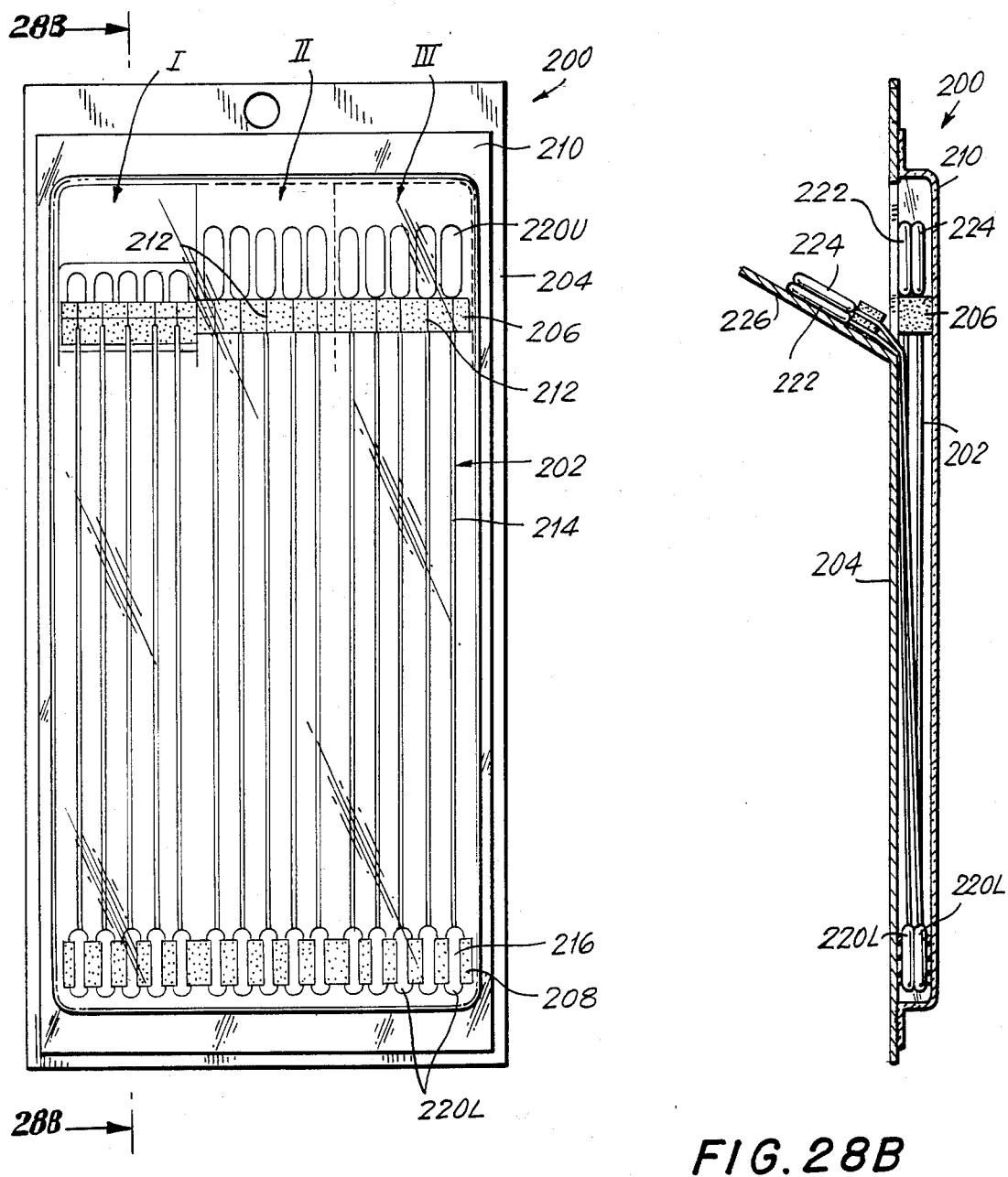

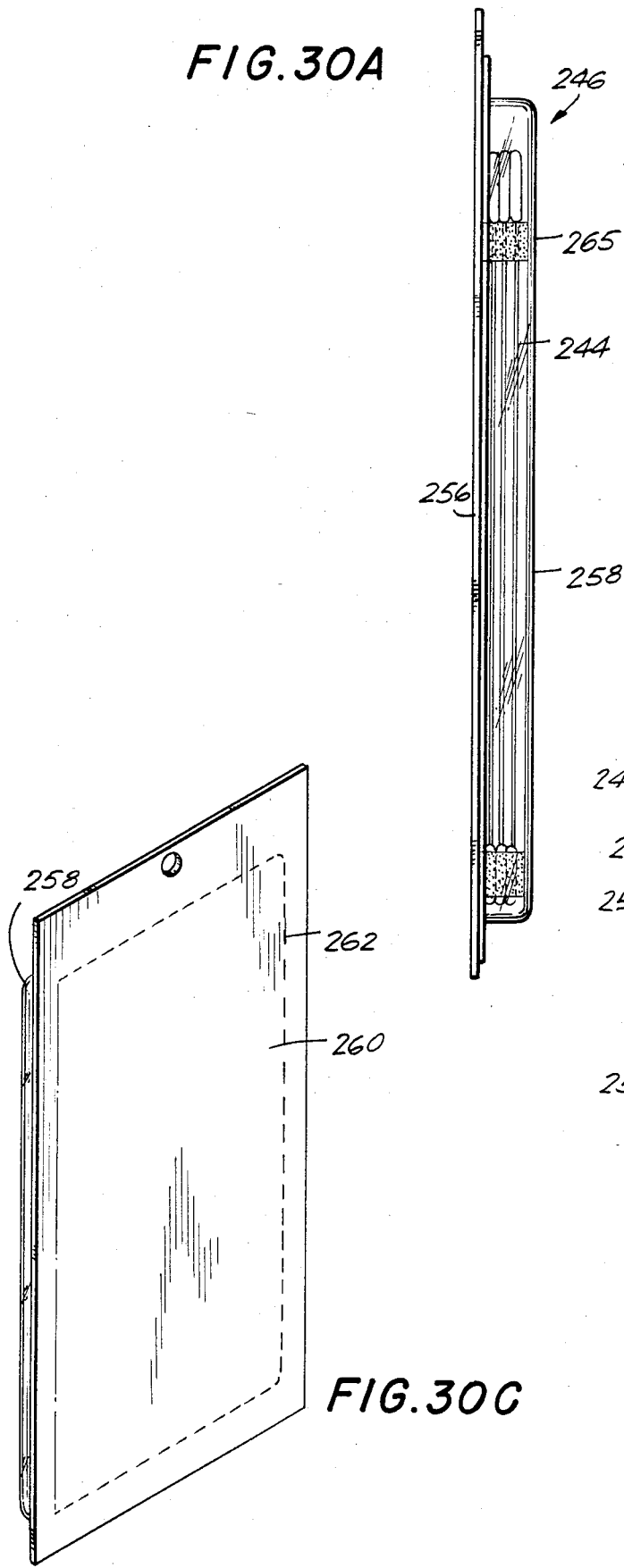
FIG.30A
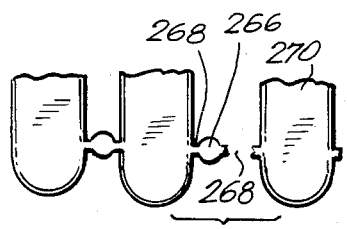
FIG.30D
FIG.30B
FIG.30C
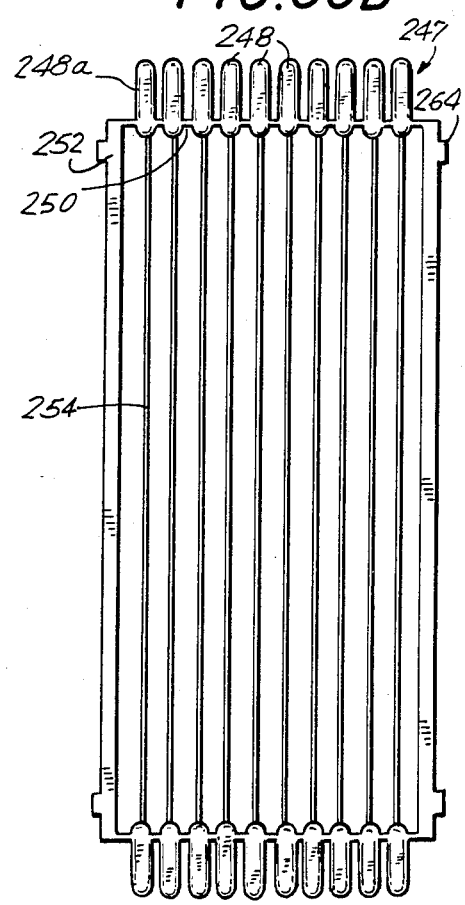

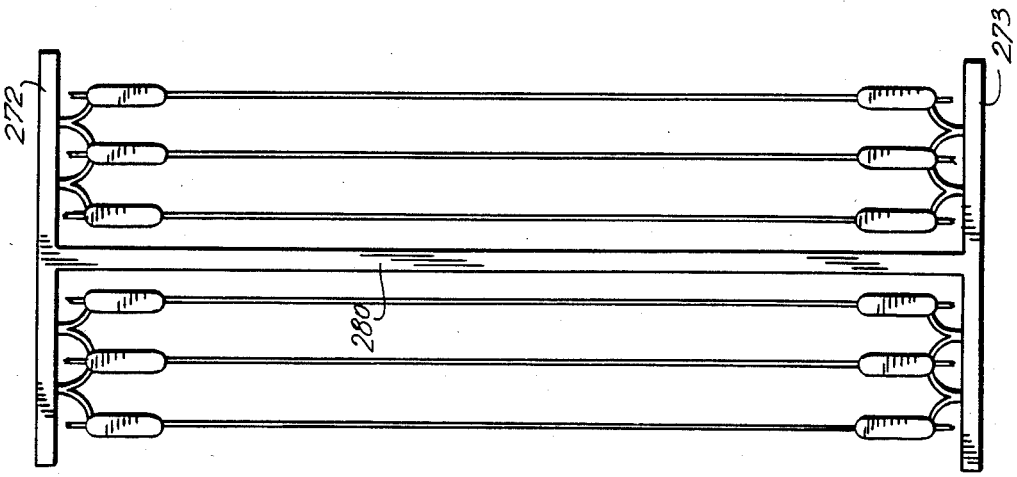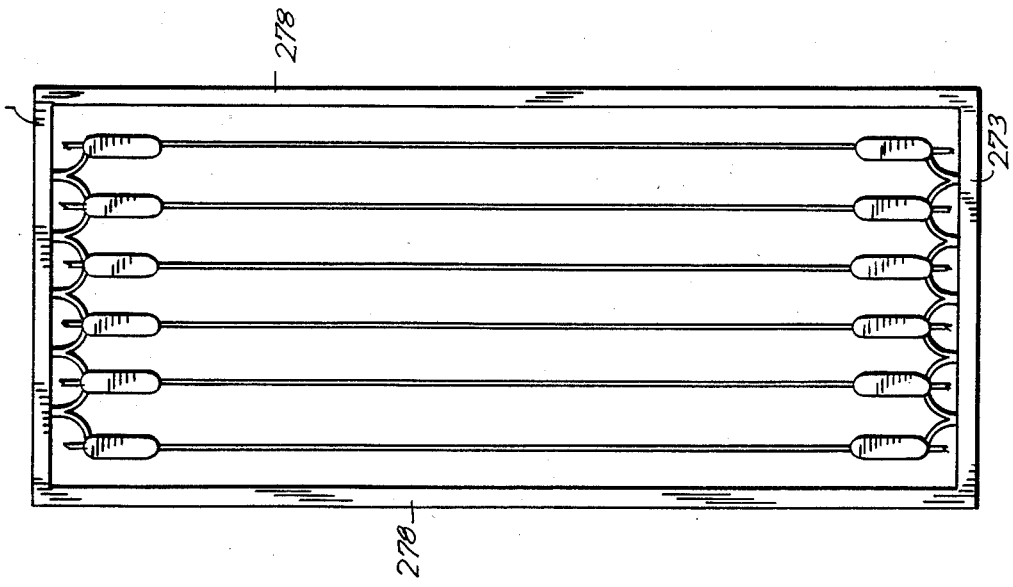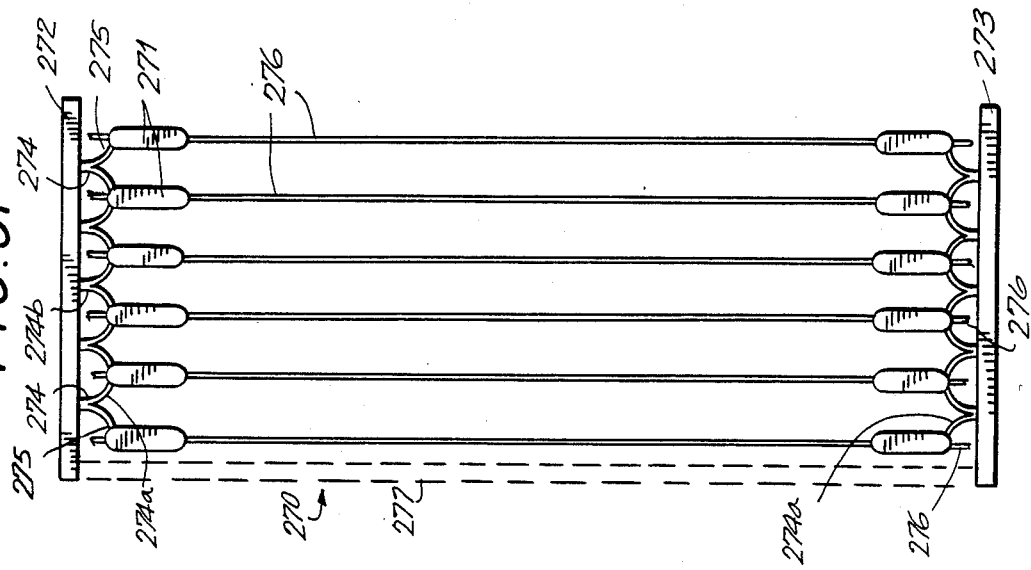

DENTAL FLOSS HOLDERS AND PACKAGE ASSEMBLY OF SAME

BACKGROUND OF THE INVENTION

This invention is in the field of dental floss holder devices of the type consisting of a strand of floss with gripping elements at each end to be held between fingers of both hands, and packages for containing a plurality of such devices and for easily dispensing such devices one-at-a-time, and methods of packaging such devices.

Despite the development of the new dental floss holder device as generally disclosed in U.S. Pat. No. 4,016,892 and the enhanced ease and efficiency of flossing when using such devices, actual availability and use by the public depends ultimately on packaging convenience plus portability and the economics of manufacture. The price of each floss unit, which has only a few inches of floss, is very low; therefore, millions must be sold to establish profitability. To manufacture devices efficiently in such quantities requires expensive mass production equipment. The cost of packaging a convenient and practical quantity, such as one to fifty of these devices, will of necessity be a high percentage of the total cost of the devices and package combined. Since these products are unique in form and no prior package design or techniques for packaging them existed, the availability and marketing of these products as new and desirable dental health apparatus has been hindered and retarded.

As noted earlier the dental floss holder devices typically are five and one half inches in total length with two half inch long gripper elements and four and one half inches in length of floss between the elements which are each approximately one eighth inch wide by one sixteenth inch thick. These gripper elements typically made of nylon or other plastic are molded onto the floss which is typically multifilament nylon, rayon, Dacron, cotton or other synthetic or natural fiber.

The floss holder devices are typically made in mass production injection molding machines which mold the gripper elements onto multiple continuous strands of floss thus producing successive adjacent flossing units, each comprising a length of floss with a pair of spaced elements, each unit adjoining or spaced about one half inch from the next element. These successive flossing units on continuous strands of floss may be separated from one another before they are packaged. According to the present invention applicant has developed new techniques and structures for mass production techniques of packaging these devices in multiple groups according to designs which are practical, feasible and economical.

SUMMARY OF THE INVENTION

This invention is a new package design and technique for holding and dispensing a plurality of dental floss holders or floss units in a practical and profitable manner which may be in parallel and in a flat place, and the units may be sequentially connected to each other or they may be separated. In a preferred embodiment the package is a vacuum formed or injection molded plastic panel which defines thereon a plurality of parallel holding means, each to receive and releasably hold one to three floss units. Each holding means may consist of a pair of recesses to receive and hold the gripping elements with a groove extending between said pair of recesses to guide and/or protect the strands of floss extending therebetween. The gripping elements are secured by friction, adhesive, or mechanical coupling or by virtue of tension in the floss. The panel or support part on which the floss units are mounted is preferably designed to be highly compact with the floss units closely parallel and the recesses or holding means being aligned and closely adjacent. The mounting surface defining these holding means is later covered or enveloped either by a second panel which is hinged to the first and protects the mounted floss units or by a closing panel that contains labelling and a means of accessing the floss units.

BRIEF DESCRIPTION OF THE DRAWINGS

FIG. 28A is a front elevation of a blister package containing a plurality dental floss devices;

FIG. 28B and 28C are left side and rear elevation views of the package of FIG. 28A;

FIG. 30A is a side elevation of another embodiment of a package of floss devices;

FIG. 30B is a front elevation of a rack of floss devices within a blister package of FIG. 30A;

FIG. 30C is a rear perspective view of the package of FIG. 30A;

FIG. 30D is a fragmentary enlarged view of the rack of FIG. 30B;

FIG. 31 is a fragmentary front elevation of another embodiment;

FIG. 32 is a fragmentary front elevation of another embodiment similar to FIG. 30B; and FIG. 33 is a fragmentary front elevation of another embodiment similar to FIG. 32.

DETAILED DESCRIPTION OF THE PREFERRED EMBODIMENTS

These drawings show a variety of embodiments of package designs and techniques for packaging a plurality of dental floss holder devices in attractive and convenient dispensers which are mechanically and economically feasible to manufacture.

Figure 1:
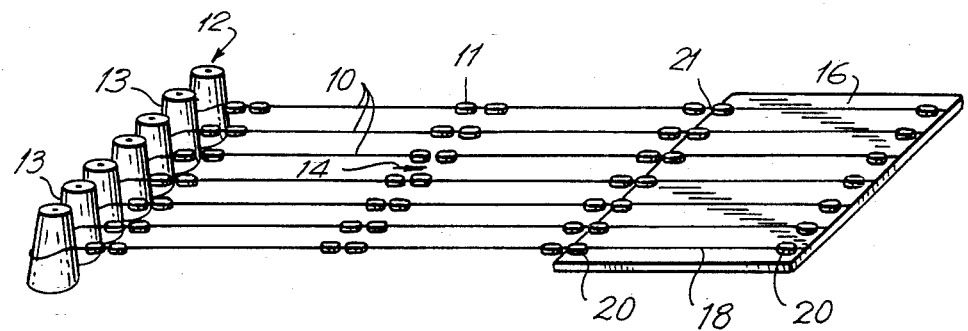
FIG. 1 is a schematic representation of continuous strands of dental floss with gripper elements secured thereon, the multiple strands being fed from a source to a single mounting board.

FIG. 1 indicates schematically how a typical continuous strand 10 of dental floss with gripper elements 11 molded thereon is fed from a source 12 which could be a supply spool or pern 13 as shown, or could be the injection molding or other machine itself where the gripping elements are originally attached to the floss. As indicated by the arrow 14 in FIG. 1 the strands 10 are moving to the right to a mounting board or support member 16 which receives and holds a plurality of individual units aligned in parallel and spaced relationship. These units, each comprising a single segment of floss 18 with a pair of grippers 20 at opposite ends, are each individually removable from the mounting board independently of the remaining elements when the product is completed. As shown these gripping elements have been freshly attached to the board and are still attached to the continuous strands 10 of the source materials. Subsequently the segments will be severed at point 21 from the source.

Figure 2:
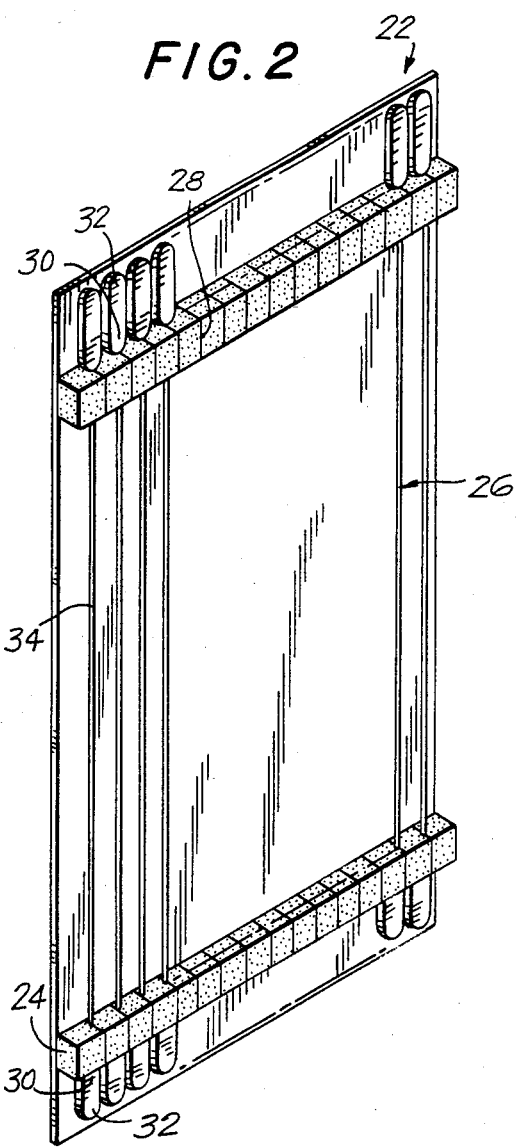
FIG. 2 is a front-perspective view of a mounting board for a plurality of gripper floss units using foam strips for attachment.
Figure 3:
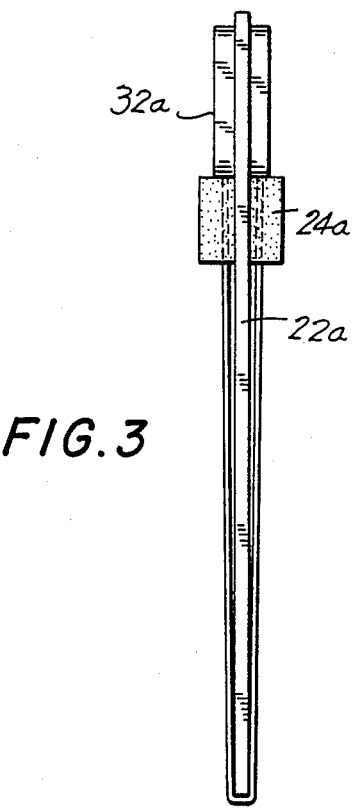
FIG. 3 is a cross-sectional view of a variation of the mounting board of FIG. 2, but having a double mounting surface.

FIG. 2 shows one embodiment of a mounting board 22 which has a pair or set of parallel foam strips 24 aligned perpendicular to the array of parallel gripping units 26. Each foam strip has a set of slits 28 adjacent the inner ends 30 of the gripper elements 32. In the assembling operation indicated generally in FIG. 1, when using a mounting board as illustrated in FIG. 2, the array of parallel supply lines of floss units would simultaneously be fed to overlie mounting board 22 at which time the floss segments 34 would be manipulated into slits 28. The result would be a very neat and compact package of a plurality of floss units securely held by the board but easily, individually removable therefrom. FIG. 3 merely illustrates a double-sided version of the board of FIG. 2 where board 22A has a pair of foam strips 24A on opposite sides and each flosser unit is wrapped about the board so that one gripper element 32A is positioned on each side of the board while the floss is held in the slits in the foam strips allowing for a package of one-half the width of the FIG. 2 board.

Figure 4:
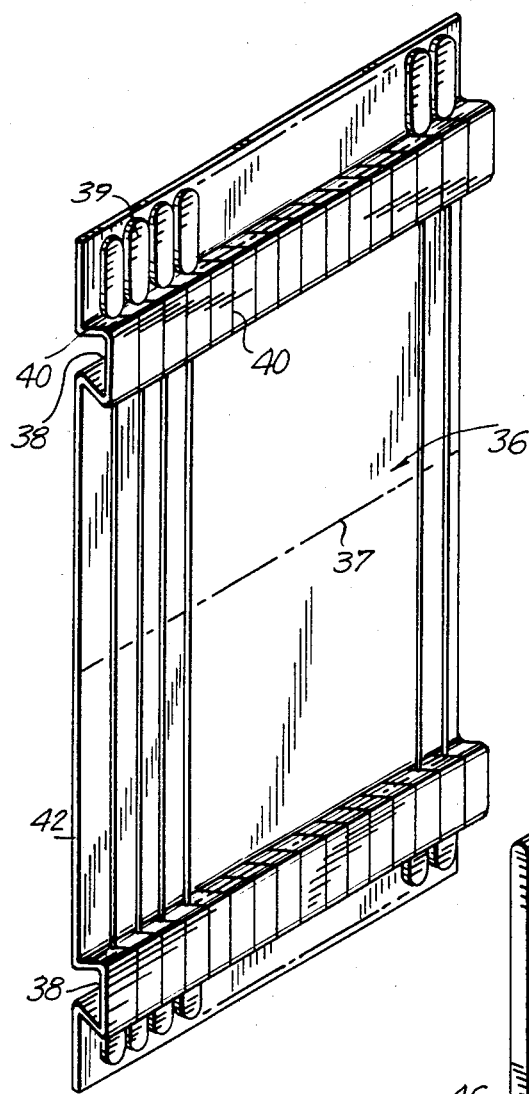
FIG. 4 is a front-perspective view of another embodiment of a one-piece mounting board for a plurality of gripper-floss units.

FIG. 4 shows another one-piece embodiment of a mounting board 36 which has raised portions 38 formed in substitution for the foam strips 24 in FIG. 2 as holding means for releasably holding said flosser units. These raised portions have slits 40 which serve the same purpose as slits 28 in FIG. 2, and accordingly the flosser units represented by sample 42 can be easily and releasably secured on the board, where each gripper element 39 is releasably engaged in the recess 42.

Figure 5:
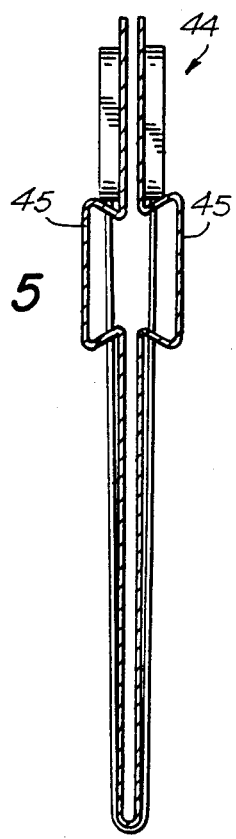
FIG. 5 is a double-sided version of the board of FIG. 4 shown in sectional view.
Figure 6:
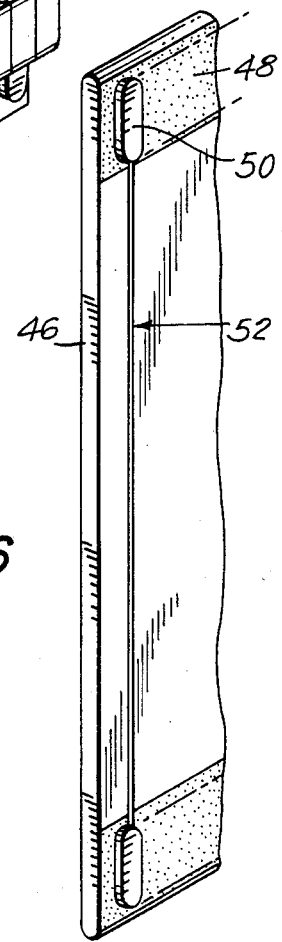
FIG. 6 is a further embodiment of a mounting board using adhesive strips for holding a plurality of gripper-floss units.
Figure 7:
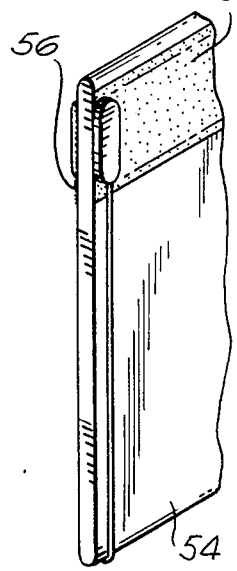
FIG. 7 is a double-sided variation of the board of FIG. 6.

FIG. 5 shows a variation 44 of the board 36 shown in FIG. 4 with a pair of raised sections 45 on opposite sides. Board 44 could be made by bending board 36 of FIG. 4 along a line 37 intermediate said raised portions to produce the design in FIG. 5. FIG. 6 shows another variation of a mounting board 46 with strips of adhesive 48 situated as parallel mounting surfaces to receive and releasably hold gripping elements 50 of floss units 52. FIG. 7 shows a variation with a mounting board 54 having the adhesive strips 56 on opposite sides of the board and the floss units wrapped around but similarly secured as in FIG. 6.

Figure 8:
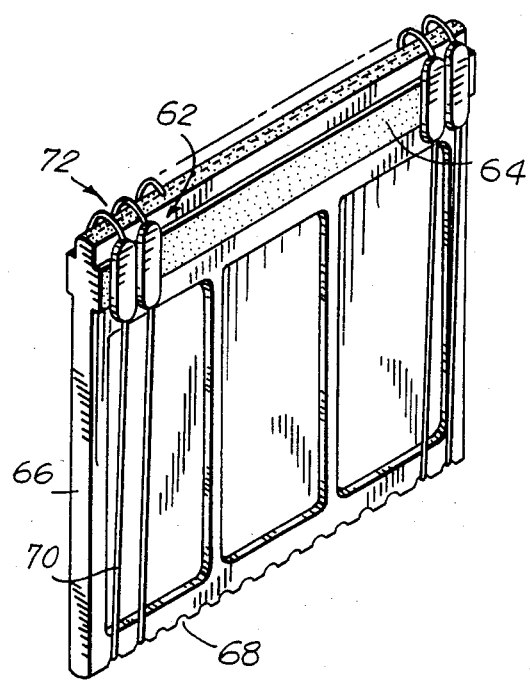
FIG. 8 is a further variation of the board of FIG. 6.
Figure 9:
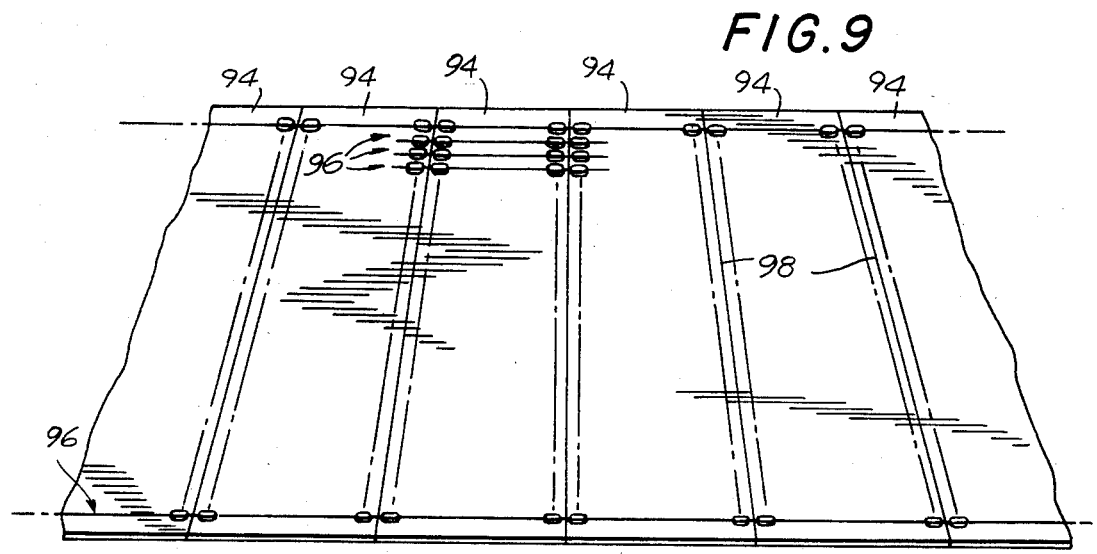
FIG. 9 shows schematically a plurality of mounting boards for receiving a plurality of continuous strands of gripping units prior to separation of such finished boards.

FIG. 8 shows gripper elements 60 with their top edges 62 extending beyond the edge of adhesive strip or bar 64 on board 66 for easier removal. Guide grooves 68 keep the floss strands 70 in proper alignment and tacky surface 72 holds the floss in place until such is cut to separate the floss units.

Figure 11:
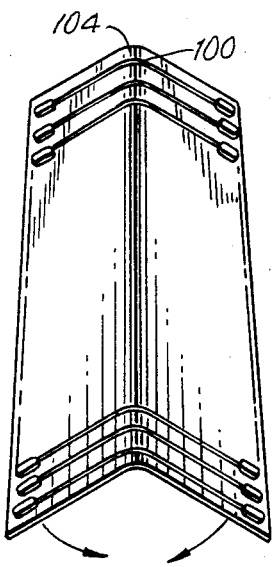

FIG. 11 correspondingly generally to FIGS. 1 and 2 except that the mounting board is a multiple board having a plurality of sections 94 which are later separated from each other. Prior to said separation, however, the continuous strands of floss 96 are fed in parallel lines to overlie board segments 94 and are secured there by any of the attachment means as exemplified in FIGS. 2 through 8. Thereafter, the boards are cut aboard along outlines 98 at which time all the strands of floss are cut along the same lines thereby completely separating each board as a finished product for final packaging.

Figure 10:
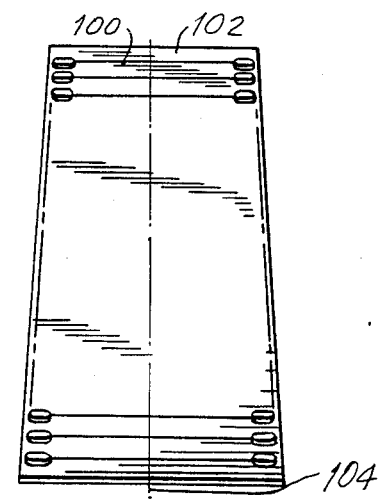
FIGS. 10, 11 and 12 show the steps of providing a single board with a plurality of parallel-positioned gripping units, folding the board to provide a core support for folded units.
Figure 12:

FIGS. 10 through 12 illustrate the steps in going from FIGS. 4 to 5, for example, whereby an array of floss units 100 are secured to a board 102 as shown in FIG. 10; then the board 100 is folded about centerline 104 as indicated in FIG. 11 to produce a finished product shown in FIG. 12 which corresponds to FIG. 5.

Figure 13:
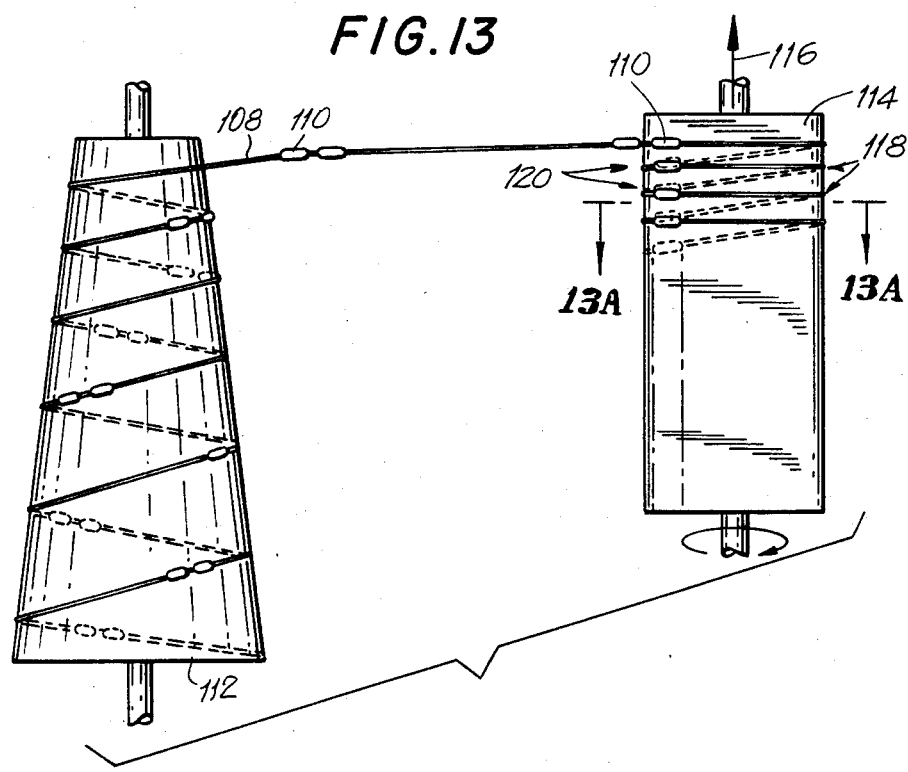
FIG. 13 shows a flat core with the gripper units wound from a source in helical loops.

FIG. 13 illustrates a substantially different packaging approach wherein the continuous strand 108 of floss with gripper elements 110 attached is fed from a source 112 which may be a master pern or may be the moulding apparatus wherein the gripper elements 10 are originally attached. A core or card 114 receives the strand 108 and rotates while being moved axially in the direction of arrow 116 until a plurality of helical loops 118 are formed with the gripping elements 110 for each loop being situated along a line on either side of the core as further illustrated in FIG. 13A. Subsequently the continuous floss may be cut along a line to sever the floss indicated at numeral 120 between each two immediately adjacent gripping elements 110. This will leave each flossing unit 118 to have its pair of elements 110 at opposite ends of the floss segment.

Figure 14:
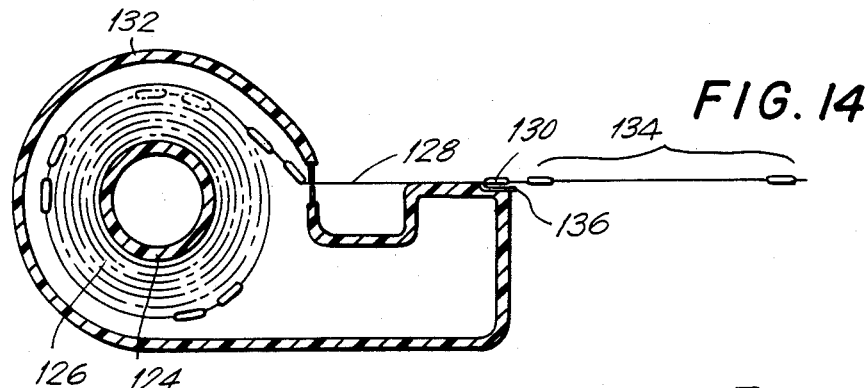
FIG. 14 shows a cylindrical core with the gripper units wound in spiral loops, the core being rotatably mounted within a dispenser housing.
Figure 14A:
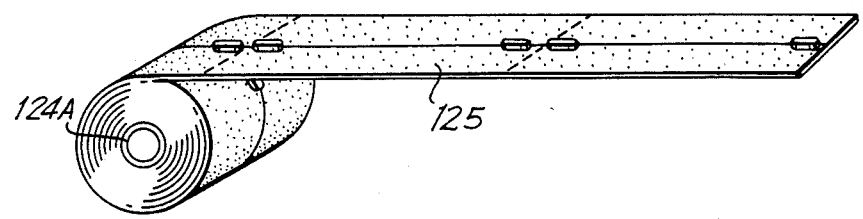
FIG. 14A shows a spirally wound tape on which is removably adhered a continuous strand of floss, this tape being mountable in the dispenser of FIG. 14.

FIG. 14 shows a still further embodiment wherein a central spool 124 has wound thereon in spiral loops of expanding diameter 126 the continuous floss 128 with the various gripping elements 130 secured thereon. This spool is rotatably mounted in housing 132, and in use the outermost floss unit 134 is pulled until it passes a cutting edge 136. After unit 134 is cut off the lead gripping element of the next floss unit remains exposed so that the user can easily pull this unit out for the next cutting operation. Element 127 is a rubber diaphragm with a split through which the floss passes. The adjacent edges of the split hold and support the exposed floss from falling or slipping back into the housing. As an alternate to spool 124 with continuous floss, FIG. 14A shows spool 124A with a strip of one sided adhesive tape 125 rolled spirally on the spool, and with the continuous strand of floss and gripping elements removably adhered to the adhesive side. As tape is uncoiled, floss units are exposed and can be cut off.

Figure 15:
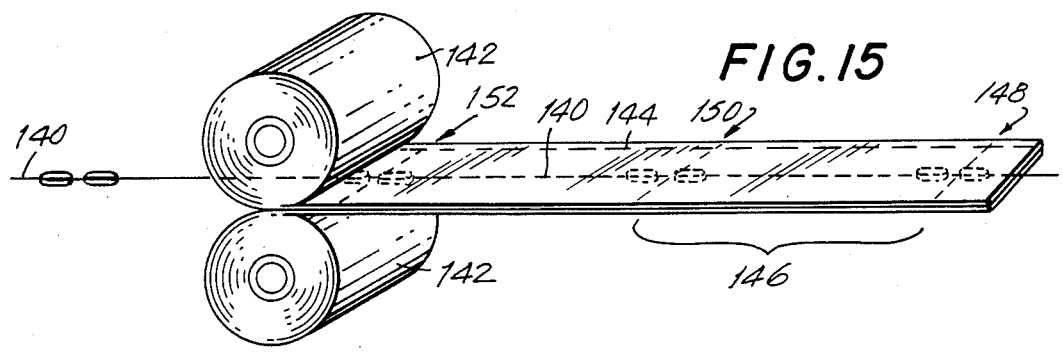
FIG. 15 shows a perspective view schematically of a continuous strand of gripper elements formed into individual sealed packages.

FIG. 15 shows one final embodiment wherein the continuous floss with floss units 140 is fed from a source not shown, and rolls of plastic or paper tape 142 are provided and fed to form a laminate or sandwich with the unit 140 captured therebetween. Subsequently, the two layers of plastic or paper tape are joined along the dotted lines 144 and optionally along lines 145 enveloping each floss unit 140, the joining being done either by heat sealing or adhesive, whichever is feasible. At an appropriate time the sandwich and sealed tape package is diecut or cut through along lines 148, 150, 152 transversely of the axis of the tape and floss, these cuts being adequate to sever the floss inside along with the package which can later be torn open when the user wishes.

Figure 16B:
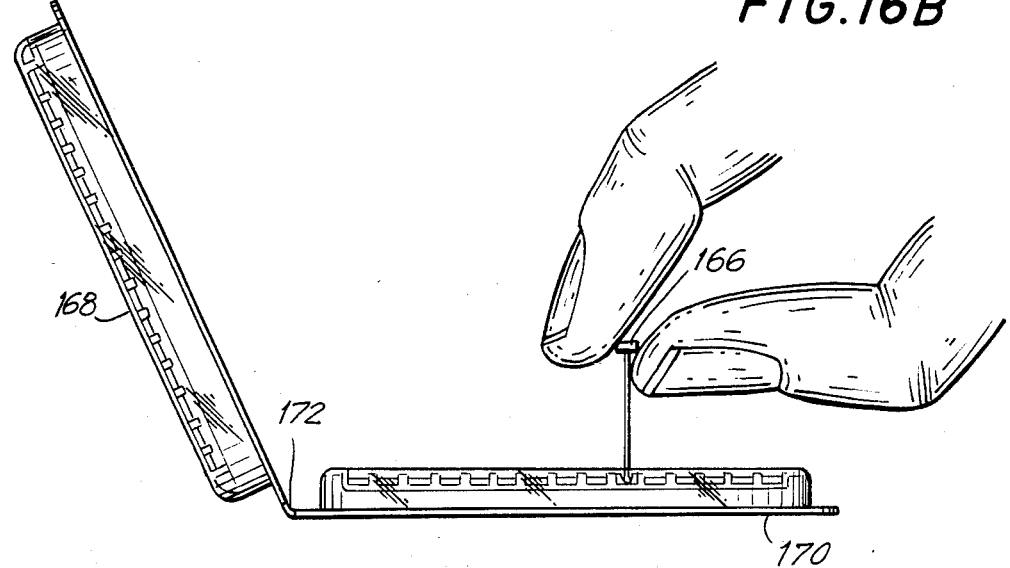
FIG. 16B is an end view of FIG. 16A in partially open condition.
Figure 16A:
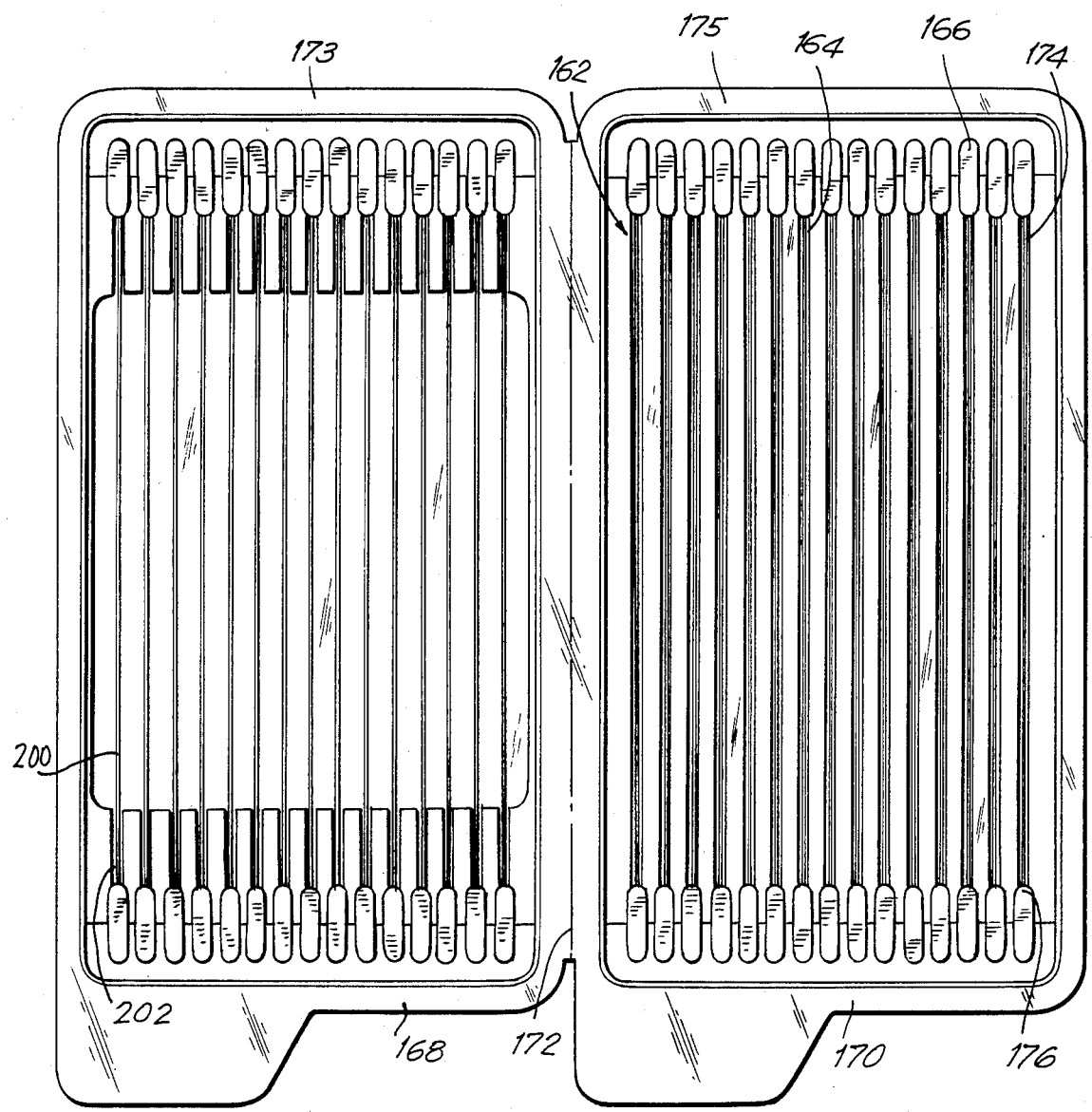
FIG. 16A is a plan view of a further embodiment of a package in open condition for holding a plurality of flossing devices.

FIG. 16A illustrates a preferred embodiment 160 of a package for holding thirty floss units 162, each comprising a length of floss 164 and opposite gripper elements 166. This package is an integrated mounting board and outer housing consisting of upper and lower formed plastic panels 168, 170 respectively foldable about line 172 as seen in FIG. 16B into the closed condition shown in FIG. 16C and 16D. Alternatively the hinge could be formed at the end shown in 16E joining edges 173 and 175. Each panel includes fifteen parallel grooves 174 visible in FIGS. 16A–16C, each terminating in opposite recesses 176. One or more floss units 164 are securely but releasably held in each groove when the gripping elements 166 are positioned in their respective recesses 176 as seen in FIG. 17, and the length of floss 164 between elements is aligned with or without tension in groove 174.

Figure 18:
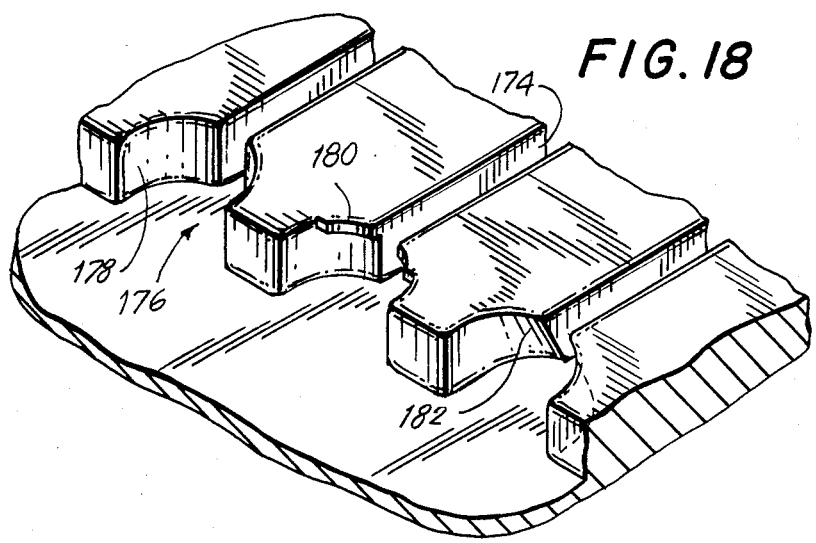
FIG. 18 is an enlarged fragmentary perspective view of recesses for engaging gripping elements.
Figure 19:
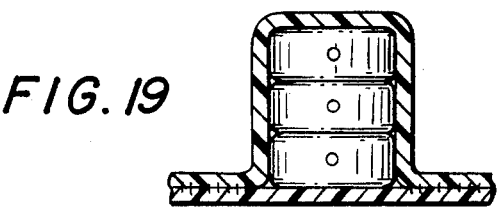
FIG. 19 is a fragmentary sectional view of another package embodiment.

FIG. 18 indicates various forms the recess may have, i.e. essentially straight walls 178, straight walls with a lip 180, or inclined walls 182. In all cases the floss units are positioned to remain engaged along a groove to the upper or lower panel with the gripping elements in the recesses until a user manipulates one element out of its recess and removes the entire floss unit. Two or three floss units could be stacked in one groove, 176 for example, which would appear as generally shown in FIG. 19.

Figure 20:
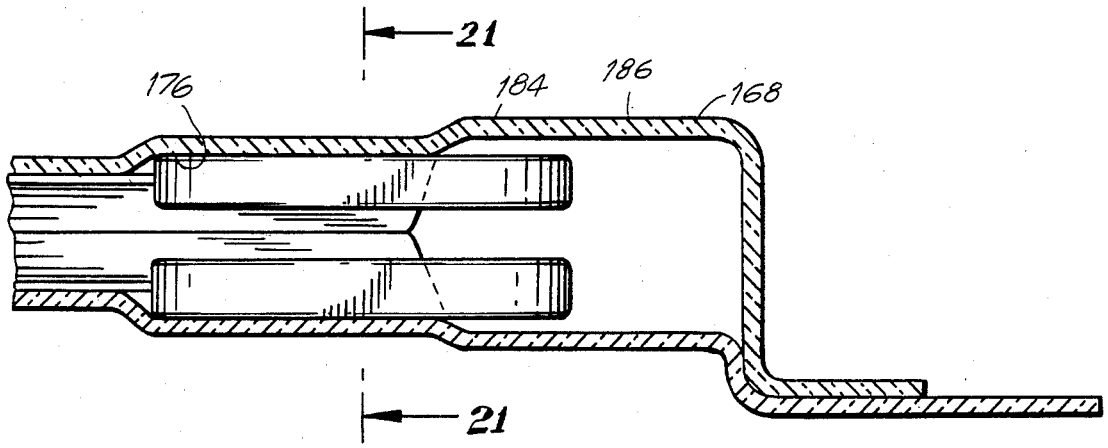
FIG. 20 is a fragmentary sectional view taken along line 20—20 in FIG. 16C.

As indicated in FIG. 20 the terminal end 184 of each recess 176 and adjacent area 186 in the upper panel 168 is displaced slightly outward from the panel floor 188 to provide greater accessibility for a person's finger tip and thumb to engage and pull a gripper element 166 out of its recess and thereby to remove a complete floss unit from the panel.

Figure 16C:
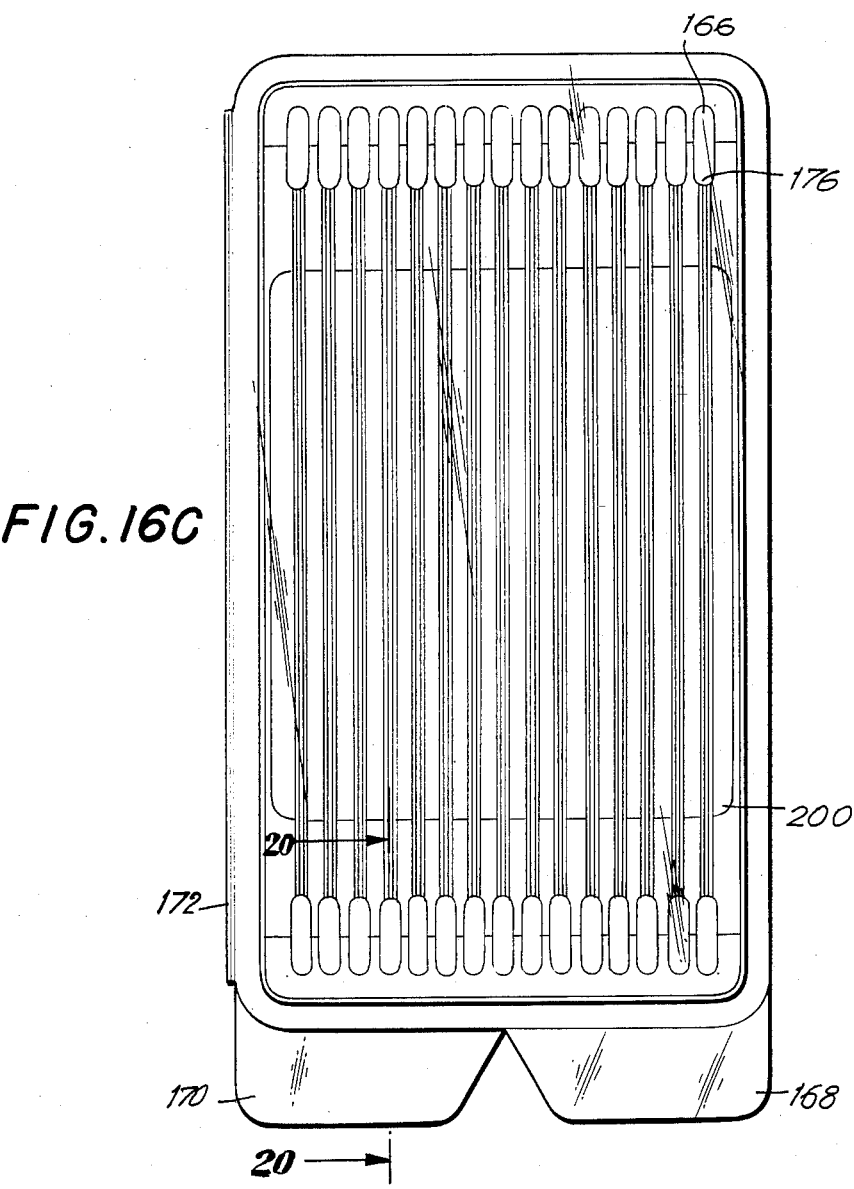
FIG. 16C is a top plan view of the package of FIG. 16A shown in closed condition.
Figure 16D:
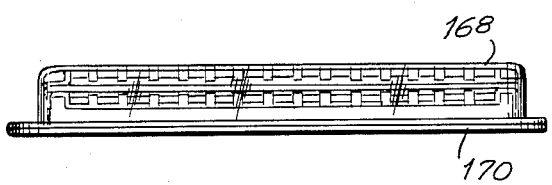
FIG. 16D is a front end elevation of the package of FIG. 16A.
Figure 16E:
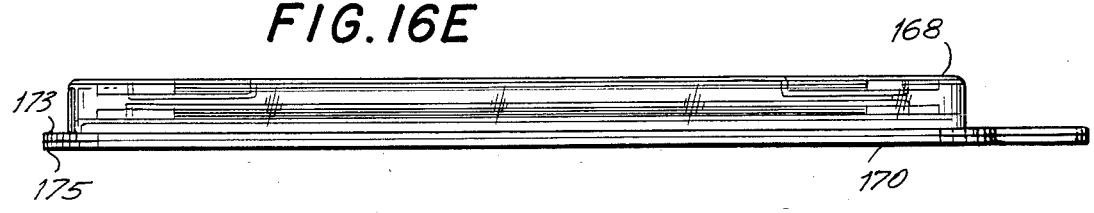
FIG. 16E is a side elevation of a variation of the package of FIG. 16A.
Figure 17:
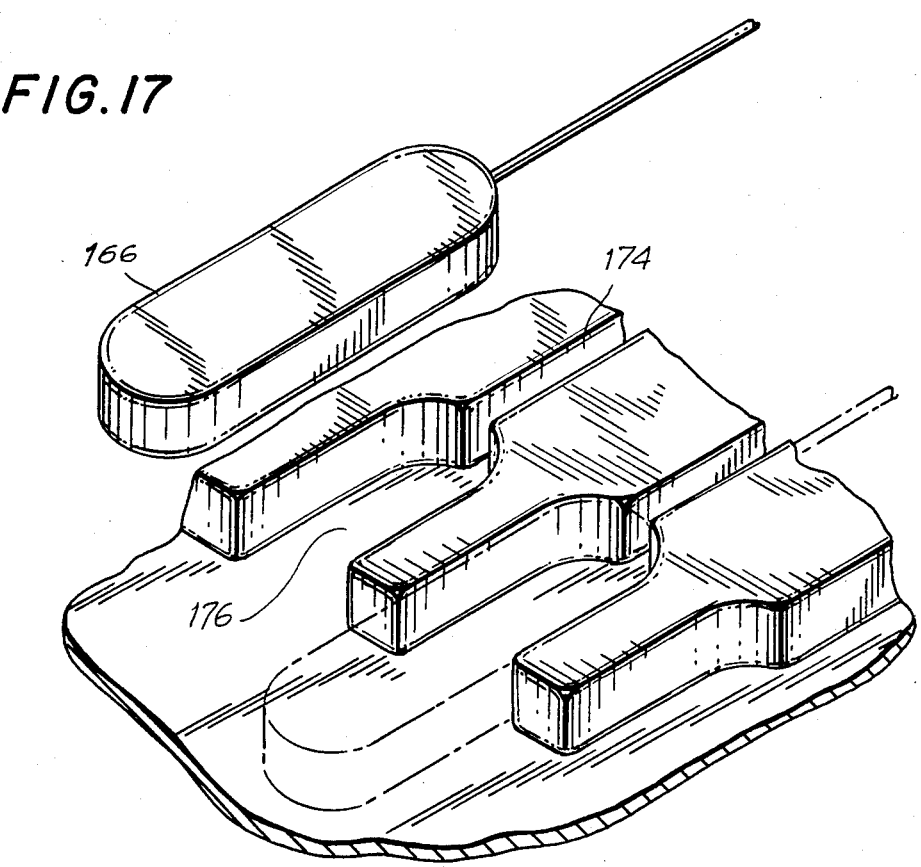
FIG. 17 is a fragmentary perspective view of a gripping element in a recess.
Figure 21:
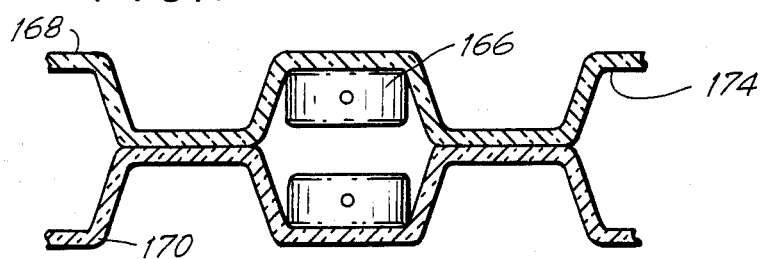
FIG. 21 is a fragmentary sectional view taken along line 21—21 in FIGS. 16C and 21.
Figure 22:
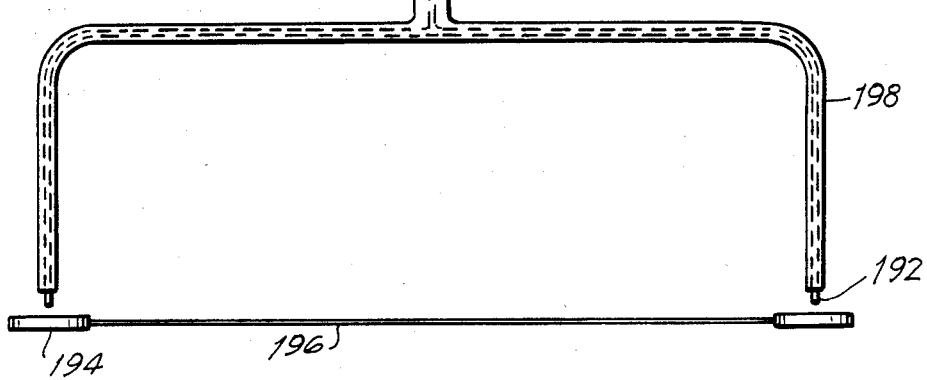
FIG. 22 is a fragmentary elevation of a component of the manufacturing apparatus.

FIG. 21 shows how adjacent floss units are situated in the upper and lower panels 168, 170 respectively when the package is in its closed condition shown in FIG. 16C. These floss units are placed on the panels by apparatus, schematically and partially shown in FIG. 22 which includes a stem 190, a pair of spaced contact points 192 which (a) engage and hold a pair of gripper elements 194 of a flosser unit 196 with the floss length extending therebetween, (b) transport said floss unit from its source or place of temporary storage to a particular groove of one of the upper or lower panels, and (c) position the gripper elements into their respective recesses with the floss length in the groove. In this apparatus the sharply pointed contact tips 192 slightly pierce, and hold the gripping elements 194 until the transport phase is completed; then the tips 192 are retracted into arms 198, thus automatically withdrawing the tips out of the gripping elements. It is contemplated that the apparatus represented in FIG. 22 would have adequate arms and/or contact points to engage fifteen floss units at once and transport and position them on a panel in essentially a single motion, since fast, efficient and economical packaging is a principal objective. Where a plurality of units are transported simultaneously from a source of continuous strands, the plurality of units are all cut at once from the source strands after the units are positioned on the panel.

As mentioned above the panels are integral parts of a single plastic sheet that is vacuum or thermo-formed or injection molded. The result is a single component that serves the multiple purposes of two mounting boards for floss units with easy dispensing of the units individually while also constituting a complete closable housing in a compact and highly esthetic and low cost structure. The package even includes on front panel 168a smooth area 200 seen in FIGS. 16A and 16C for placement of a label. This area interrupts and shortens the grooves 202 in FIG. 16A, but allows a label to be placed in the area before the floss units are attached.

Figure 23:
FIG. 23 is a fragmentary sectional view similar to FIG. 21 of another packaging embodiment.

The plurality of parallel continuous strands each formed as successive floss units can be drawn together to a stationary mounting board or to a moving board or a revolving spool on which the units are releasably secured. The floss may be selected from many types including waxes, unwaxed, wide, fine, flavored, impregnated, etc. Also the gripper elements can have variable shape from the smooth pellets shown to notched styles where the notch or aperture releasably engages a projection on the mounting board or cylindrical core on which the units are attached. The one-piece package is particularly efficient and inexpensive to manufacture since it includes the front or upper and rear or lower panels and the living hinge integral with and joining the panels, this hinge being capable of a great number of bends without fracturing. It is also possible with this type of package to design each groove and its two recesses to be deep enough to hold two or three layers of flosser units, the upper unit being removable without the lower units. If these two or three layers are on the lower panel, the upper panel could contain additional layer(s) of units or be void of flossers or be a flat mounting card or panel as indicated in FIGS. 23 and 19.

Figure 13A:
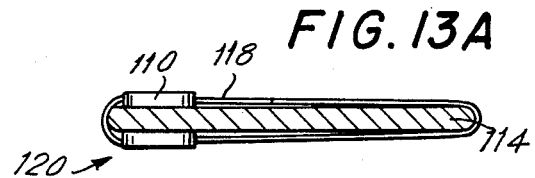
FIG. 13A shows a top end view of the core of FIG. 13.

Another package design which is a variation from that of FIGS. 13, 13A and FIG. 7, is shown in FIGS. 24-27 where adjacent gripping elements 190 and 192 of floss unit 191 and 193 respectively are initially joined when molded. These adjacent and abutting elements are breakable along their common junction line 194 to form separate floss units such as 191 and 193, each comprising a single strand of floss 196 and opposite gripping elements. The area of junction between each two adjacent abutting elements may be reduced in cross-sectional area, or otherwise weakened relative to the elements 190, so that said junction will easily break apart when these abutting elements are bent relative to each other along said line.

Figure 24:
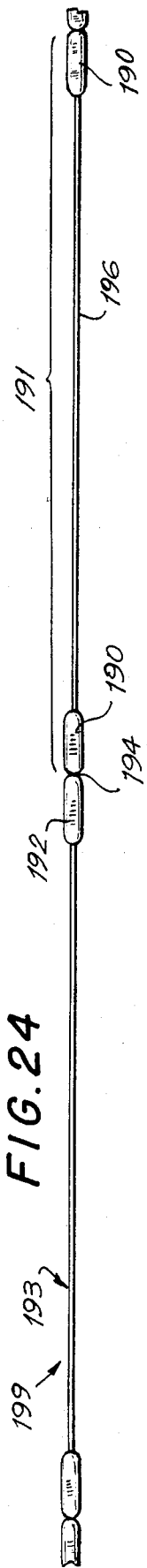
FIGS. 24 and 25 are top plan and front elevation views respectively of a further embodiment of dental floss holders.
Figure 25:
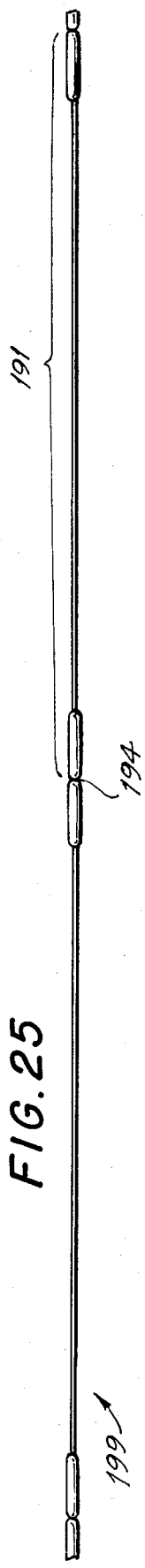
Figure 26:
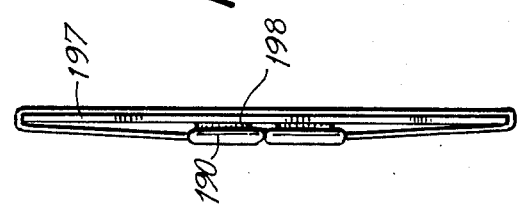
FIG. 26 and 27 are front and end elevation views respectively of a package of floss holders of FIG. 25.
Figure 27:
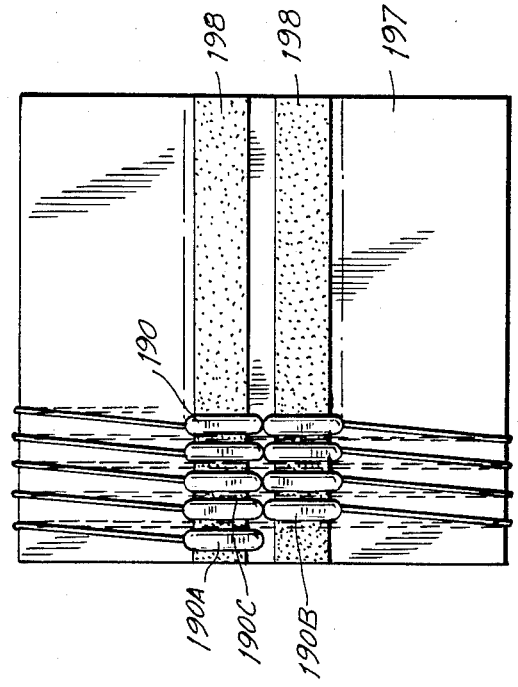

One practical arrangement for packaging and dispensing the floss units of FIG. 24 is shown in FIGS. 26 and 27 where a mounting card 197 has a pair of exposed adhesive strips 198 extending lengthwise, with the continuous strands 199 of floss units of FIG. 24 wound about the card generally helically, with the gripping elements 190 adhered to the adhesive strips 198. A user will grasp element 190A, for example, unwrap strand 196A, and then bend element 190B relative to element 190C until they break apart at about a 90 degree bend angle.

A number of practical, economic and attractive arrangements or embodiments for packaging the dental flosser devices disclosed herein are shown in FIGS. 28A through 30D. Each arrangement provides a means: (a) for holding a plurality of dental floss devices with the floss segments essentially straight and parallel to each other, (b) for displaying the devices while protecting and covering them, and (c) for dispensing these devices one at a time. If all these features are not achieved simultaneously, plus the feature of economy per unit in very high volume packaging and favorable esthetic appearance, the products will not be a commercial success. Furthermore, if packaging in a high speed, high volume manner is not achieved, these products cannot be produced to sell at a very small cost per unit, which is also essential if the products are to be made and sold at all. The packaging arrangements and techniques shown herein make the above-described objectives possible.

Figure 28C:
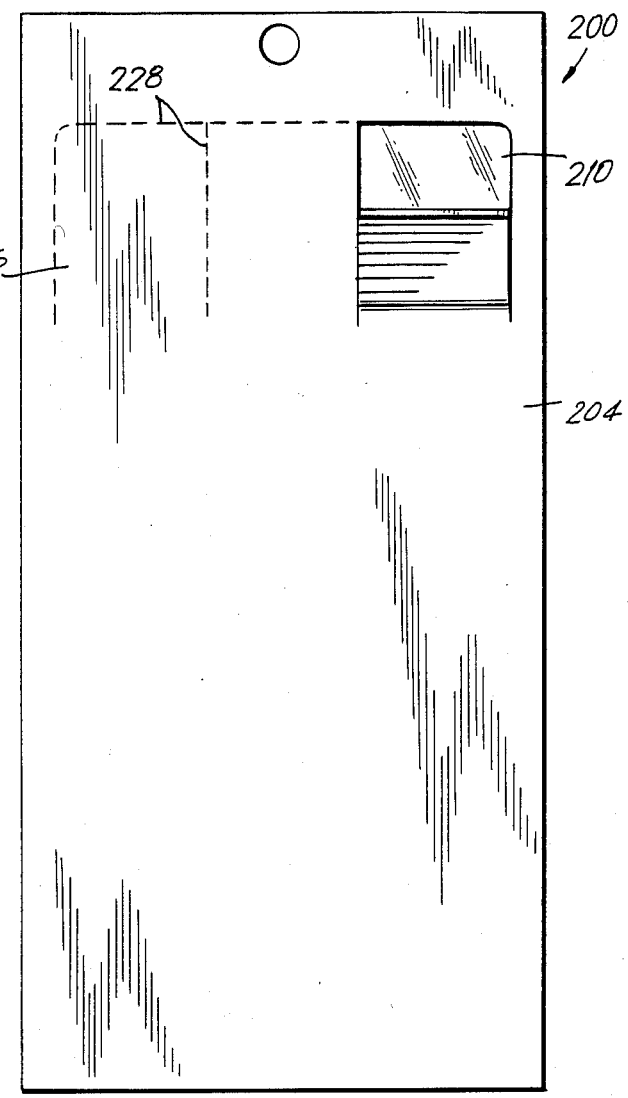

FIGS. 28A-28C show the front, side and rear of a blister package 200 containing thirty "Gripper Floss" dental floss devices 202. The package comprises a backcard 204, upper and lower foam strips 206, 208, the floss devices 202, and a polyethlene blister sheet 210. The foam strips, more clearly shown in FIG. 28D, are adhered to the backcard by adhesive, the upper strip 206 having a plurality of parallel slits 212 in which the floss 214 can extend. The lower foam strip or bar 208 has slots 216 in which a lower gripper elements 220L can be releasably engaged by walls of the slot which become slightly compressed when the element is inserted.

In the packaging process, after the foam strips are adhered to the backcard 204, the floss devices 202 are situated in three groups, I, II, and III, of five devices defining an inner layer 222, over which is placed a similar outer layer 224 of these devices. Thus a typical Group I has two layers of five devices totally ten. Each device is extended lengthwise and held securely with its lower gripper element 220L frictionally held by the compressed foam slot walls and its upper element 220U positioned above the upper foam strip 204 with the adjacent section of floss situated snugly in the slit 212. Removal of the device is achieved by engaging upper element 220U between the user's fingers, lifting it away from the backcard 204 so that the floss is lifted out of slit 212, and then pulling the element 220U and floss 214 lengthwise until element 220L is pulled through and out of and free of slot 216.

Initially this package is opened by breaking open one flap 226 along perforated line 228, exposing upper elements 220U of one group of ten devices. When not in use the opened flap can be bent back into its initial position, whereby the package will be closed and the devices covered and protected.

Figure 28E:
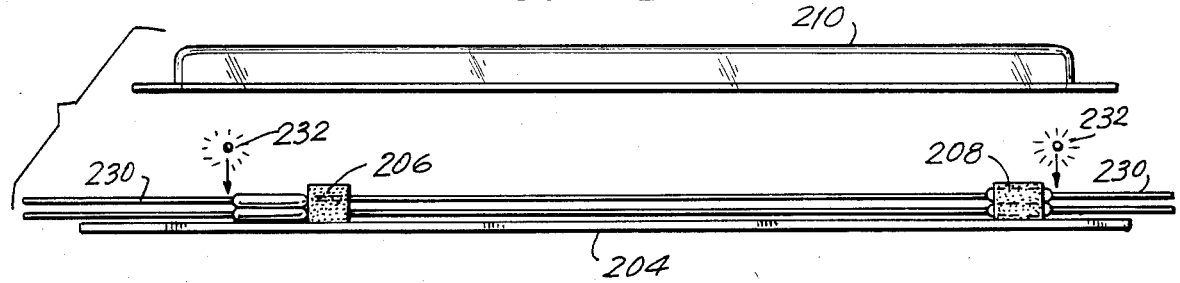
FIG. 28E is an exploded side view of a step in the process of assembling the package of FIG. 30A.
Figure 28D:
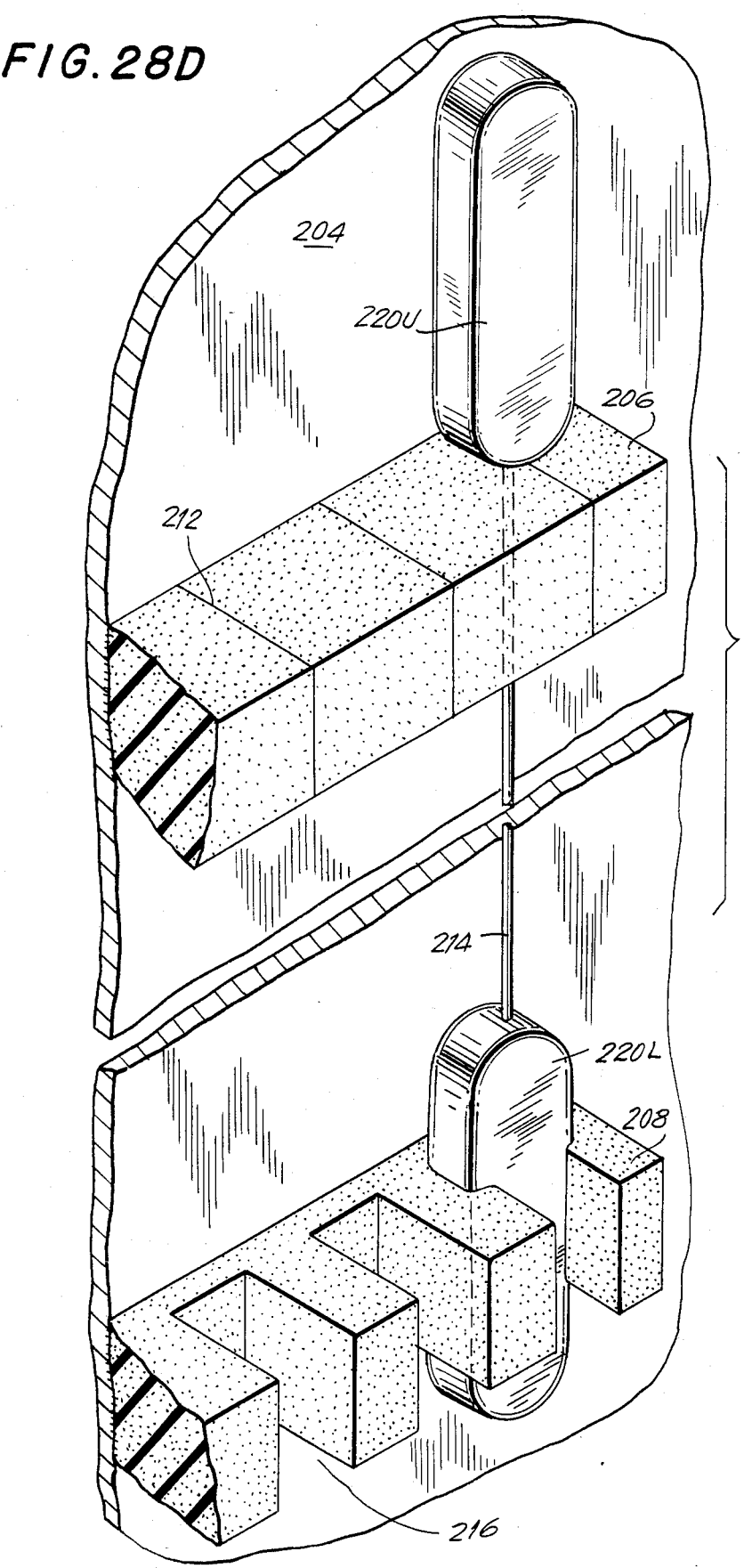
FIG. 28D is a fragmentary exploded view of FIG. 28.

During packaging, after inner and outer layers of the floss devices are positioned as seen in FIG. 28E, excess floss and/or runners 230 formed during the manufacturing process, are removed by burning with a hot wire 232. Finally the transparent blister sheet 210 is placed upon the front of the loaded backcard and sealed thereon.

Figures 29A, 29B:
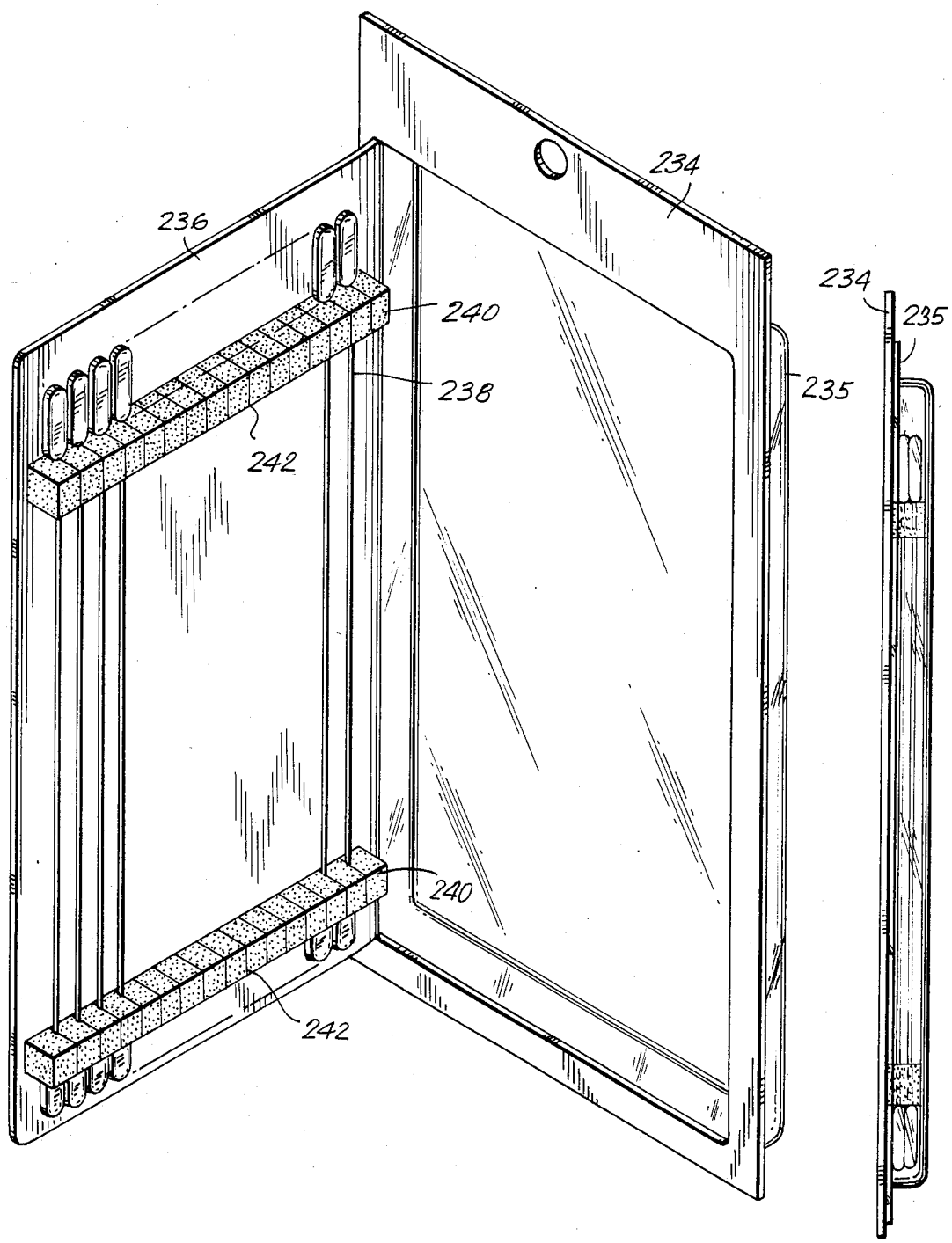
FIG. 29A is a rear perspective view of a variation of the package of FIG. 30A.
FIG. 29B is a side elevation thereof.

A variation of the package embodiment of FIG. 28A is seen in FIGS. 29A and 29B, where backcard 234 has a flap 236 which opens along a vertical bend line 238 to expose complete individual flosser devices, as contrasted to FIG. 28A where only the upper ends of the devices are exposed. In FIG. 29A there are a pair of foam strips 240, each having slits 242 in which the floss is engaged. When the panel 236 is open, each device is removed merely by holding one or both gripping elements and pulling the segment of floss out of corresponding slits. Front cover 235 is similar to that of FIG. 28A.

FIG. 30A shows a third variation of floss devices 244 in a blister package 246. The devices are formed preferably by injection molding as an array or rack 247 seen in FIG. 30B where each element 248 is joined to the adjacent element by a runner, gate or subgate 250 of the same plastic used to form the element. Along one or both sides of the array is a support bar 252 also formed of the same plastic and contiguous with the nearest gripper element 248a, for example. Each bar 252 combined with the small junctions 250 between adjacent gripping elements adds stability to the array of floss units, such that the strands of floss 254 are maintained generally straight and parallel.

To manufacture each array an appropriate injection mold is used which produces the entire array, bar or bars and junctions with each injection cycle, by known molding techniques and apparatus, samples of which are disclosed in U.S. Pat. Nos. 4,016,892, 4,006,750, 2,180,522 and 2,187,899.

After arrays of floss devices are made, three arrays or layers of ten devices each are placed adjacent the front surface of the backcard 256, and the blister cover 258 is sealed thereto. Subsequently, access door 260 as seen in FIG. 30C may be opened by breaking the backcard along perforation line 262, and a floss device may be broken off the array by bending a pair of exposed gripping elements at their junctions 250 with adjacent elements. If both support bars 252 are in place, one will have to be broken off before the first pair of gripper elements can be broken off. A tab 264 is molded onto the array; later when the array is placed in the blister package, each tab engages a slot or groove represented by 265 in the cover which orients and maintains the card in its proper position. For ease of breaking one gripping element from another, FIG. 30D shows the runner or connector 266 with a reduced diameter section 268 that will break off close to element 270.

Further embodiment of a rack-type array of floss devices is indicated as 270 FIG. 31 where gripping elements or grippers 271 are connected top and bottom rails 272, 273 respectively via connecting posts or connectors 274 which are adapted to break off the gripper at a point 275 relatively close to the gripper. Each connector has a base 274b attached to a rail and a pair of fingers 274a extending from the base to the gripping elements 271. The two rails are maintained apart and the floss strands 276 are maintained straight and separated by one or more stabilizing rails 277 indicated in dotted line.

In the manufacturing and packaging process, when a rack as shown is created, the floss strands 276 extending from each gripper to a rail, are severed but the connecting posts 274 and connecting fingers 274a are left to support and help maintain the floss devices in the stable rack arrangement. In this way the stable racks can be moved, stored, and put in packages of various shapes without risk of the floss strands of various units becoming entangled with each other, while simultaneously allowing for individual floss units to be easily broken off the rack without disturbing the remaining devices.

Regardless of exactly which connectors are selected to attach the grippers to the rack, the rack arrangements may be varied as suggested in FIGS. 32 and 33, whereby the stabilizing rails are varied in position and orientation. In FIG. 32 top rail 272 is supported by one or two side rails 278 which together like a picture frame support all the floss units not broken off the array. FIG. 33 shows a single, central rail 280 for stabilizing top and bottom rails 272 and 273.

As indicated above, many variations in form and material are possible for the invention herein disclosed within the scope and spirit of the claims appended hereto.

I claim:

1. An assembly of dental floss holders, where each holder comprises a strand of dental floss having opposite first and second ends and a pair of first and second plastic gripping elements respectively secured to each of said ends, said assembly comprising a plurality of said holders situated in spaced parallel relationship, the strand and gripping elements of each holder extending axially in a generally straight line, each of said first gripping elements being joined to other first gripping elements immediately adjacent thereto, each of said second gripping elements being joined to other second gripping elements immediately adjacent thereto, said assembly further comprising at least one generally stiff first support means having a body part and opposite ends, said support means situated generally parallel to the strand of one of said holders with said ends of said support joined to said first and second gripping elements respectively, whereby said first support means maintains said first gripping elements spaced apart from said second gripping elements of each pair respectively and maintains said strand between each pair of first and second gripping elements generally straight, each holder being separable from an adjacent holder by breaking off one gripping element relative to the adjacent gripping element joined to said one gripping element.

2. An assembly according to claim 1 further comprising junction means joining each two mutually adjacent first gripping elements and second gripping elements.

3. An assembly according to claim 2 wherein said first and second gripping elements are injection molded plastic and each of said junction means comprises injection molded plastic the same as and contiguous with said gripping elements.

4. An assembly according to claim 3 wherein each of said junctions has a central part and has end parts immediately adjacent a gripping element, said end parts having crosssectional area substantially less than that of said central part, whereby, when said junction is bent, an end part will break more readily than said central part.

5. An assembly according to claim 1 wherein said first support means comprises a rod oriented generally parallel to said strands.

6. An assembly according to claim 5 wherein said holders lie in a plane, with first and last holders defining opposite left and right sides of said plane, and said first support means lies in said plane adjacent said first holder, said assembly further comprising a similar second support means in said plane adjacent and joined to said last holder.

7. An assembly according to claim 1 wherein said first gripping elements of said plurality of holders lie in a first line which extends transversely of said strands, and said second gripping elements of said holders lie in a second line parallel to the first line.

8. A package comprising an assembly according to claim 1 and a container comprising a generally stiff panel having front and rear sides and a tab portion bendable as a door rearward out of the plane of said panel leaving an opening, and a transparent cover secured to the front side of said panel, whereby said assembly of holders is secured between said front side of said panel and said cover, and individual holders are removable from said percentage when said tab is bent rearward exposing a holder to be separated from adjacent holders.

9. A package according to claim 8 wherein said first support means comprises a rod oriented generally parallel to said strands.

10. A package according to claim 9 wherein said rod comprises a projection extending transversely away from said holders, said cover includes a groove corresponding to and for receiving and guiding therein said projection, whereby said assembly's orientation in said package is established and maintained by said projection in said groove.

11. A package containing a plurality of dental floss holders, each holder formed of a strand of dental floss with upper and lower gripping elements secured on opposite ends of said floss, said upper gripping element and a portion of said strand of floss immediately adjacent thereto defining the upper part of the holder, said lower gripping element and a portion of said strand of floss immediately adjacent thereto defining the lower part of the holder, each holder having length L when extended lengthwise, said package comprising a panel that is generally stiff and flat, has front and rear surfaces with length at least as great as L, said front and rear surfaces having upper and lower parts, a plurality of spaced-apart upper holding means on said upper part of said front surface, each upper holding means adapted to releasably engage at least a portion of said upper part of the holder, a plurality of lower holding means on said lower part of said front surfaces, each lower holding means aligned with one upper holding means and each adapted to releasably engage at least a portion of said lower part of the holder, and a cover sheet secured to said front surface and covering said plurality of holders secured thereto, said panel having at least one flap portion bendable rearward out of the plane of said panel to expose upper gripping elements, whereby a user can grasp and pull an exposed upper gripping element to release and remove the corresponding holder from said upper and lower holding means and from said package.

12. An assembly according to claim 5 wherein said parallel strands define a succession of parallel lines from first to last, and said support means is situated approximately midway between said first and last strands.

13. An assembly according to claim 5 wherein said parallel strands define a succession of parallel lines from first to last, and said support means is situated outward and adjacent said first strand.

14. An assembly comprising a dental floss holder which comprises a strand of dental floss extending generally straight and having opposite first and second ends and a pair of first and second plastic gripping elements respectively secured to each of said ends, and (b) a generally stiff support means extending generally parallel to said strand and having its ends respectively joined to said first and second gripping elements, whereby said support means maintains said first gripping element spaced apart from said second gripping element and maintains said strand between said first and second gripping elements generally straight, said holder being separable from said support by breaking off each of said gripping elements from said support.

15. An assembly of dental floss holders, where each holder comprises a strand of dental floss having opposite first and second ends and a pair of first and second plastic gripping elements respectively secured to each of said ends, said assembly comprising a plurality of said holders situated in spaced parallel relationship, the strand and gripping elements of each holder extending axially in a generally straight line, said assembly further comprising a pair of generally parallel spaced apart support rails, said plurality of holders situated between said rails and generally perpendicular to them, said assembly further comprising a series of spaced apart connectors, each connector having a base at one end joined to one of said rails and a pair of fingers at the other end, each connector located such that its pair of fingers are adjacent two gripping elements of adjacent holders, with each finger joined to one of said gripping elements, said assembly further comprising at least one generally stiff support means extending between and having its ends joined to said rails, whereby said support means maintains said rails spaced apart and thereby maintains each pair of first and second gripping elements and strand of floss therebetween generally straight, each holder being separable from the assembly by breaking off each of its gripping elements from said connector finger to which it is attached.

16. An assembly according to claim 15 wherein all said first and second gripping elements are injection molded plastic, and each of said connectors comprise injection molded plastic the same as and contiguous with said gripping elements.

17. An assembly according to claim 16 wherein each of said fingers has a minimum cross-sectional area substantially less than that of said base, said holder being separable from said assembly when the gripping elements thereof are bent relative to the connector fingers to which they are joined, and break off at said smaller cross-sectional area.

18. An assembly according to claim 15 wherein said support means comprises a rail oriented generally parallel to said strands.

19. An assembly according to claim 15 wherein said holders lie in a plane, with first and last holders defining opposite left and right sides of said plane and said support means lies in said plane adjacent said first holder, said assembly further comprising a second support means in said plane adjacent and joined to said last holder.

20. An assembly according to claim 15 wherein said holders lie in a plane, with first and last holders defining opposite left and right sides of said plane, and said support means lies in said plane and is situated between two adjacent holders and generally midway between said first and last holder.

21. An assembly of dental floss holders, where each holder comprises a strand of dental floss having opposite first and second ends and a pair of first and second plastic gripping elements respectively secured to each of said ends, said assembly comprising a plurality of said holders situated in spaced parallel relationship, the strand and gripping elements of each holder extending axially in a generally straight line, said plurality of first elements defining a generally straight line, said plurality of second elements defining a generally straight second line, each two adjacent first elements being joined together by a connector a portion of which has a minimum cross section that is less than the minimum cross section of each of said elements, each element that is joined to an adjacent element being separable therefore by bending and breaking said connector at said portion of minimum cross section.

* * * * *